(12) United States Patent
Nasry (10) Patent No.: US 10,820,857 B2
(45) Date of Patent: Nov. 3, 2020

(54) HOME MEDICAL EXAMINATION SYSTEM AND GARMENT (71) Applicant: Samer Nasry, Franklin, MI (US)

(72) Inventor: Samer Nasry, Franklin, MI (US)

(*) Notice: Subject to any disclaimer, the term of this patent is extended or adjusted under 35 U.S.C. 154(b) by 35 days.

(21) Appl. No.: 16/265,339

(22) Filed: Feb. 1, 2019

(65) Prior Publication Data
US 2019/0231262 A1 Aug. 1, 2019

Related U.S. Application Data (60) Provisional application No. 62/625,070, filed on Feb. 1, 2018, provisional application No. 62/677,552, filed
(Continued)

(51) Int. Cl.
| | |
|---|---|
| A61B 5/00 | (2006.01) |
| A41D 1/00 | (2018.01) |
| A61B 5/0205 | (2006.01) |
| A61B 5/0408 | (2006.01) |
| A61B 7/02 | (2006.01) |
| A61B 7/04 | (2006.01) |
| A61B 7/00 | (2006.01) |
| A61B 1/227 | (2006.01) |
| A61B 1/24 | (2006.01) |
| A61B 3/12 | (2006.01) |
| A61B 5/1455 | (2006.01) |
| H04R 1/08 | (2006.01) |
| H04R 1/40 | (2006.01) |

(Continued)

(52) U.S. Cl.
CPC ............ *A61B 5/6804* (2013.01); *A41D 1/005* (2013.01); *A61B 1/227* (2013.01); *A61B 1/24* (2013.01); *A61B 3/12* (2013.01); *A61B 5/0006* (2013.01); *A61B 5/0013* (2013.01); *A61B 5/0024* (2013.01); *A61B 5/0205* (2013.01); *A61B 5/04085* (2013.01); *A61B 5/14551* (2013.01); *A61B 5/4824* (2013.01); *A61B 5/7264* (2013.01); *A61B 5/7425* (2013.01); *A61B 5/7465* (2013.01); *A61B 7/003* (2013.01); *A61B 7/008* (2013.01); *A61B 7/026* (2013.01); *A61B 7/04* (2013.01); *G16H 80/00* (2018.01); *H04R 1/08* (2013.01); *H04R 1/406* (2013.01); *H04R 3/005* (2013.01); *A61B 5/02233* (2013.01); *A61B 5/6831* (2013.01); *A61B 5/6843* (2013.01); *H04R 2201/023* (2013.01)

(58) Field of Classification Search
CPC combination set(s) only.
See application file for complete search history.

(56) References Cited

U.S. PATENT DOCUMENTS

| | | |
|---|---|---|
| 7,156,808 B2 | 1/2007 | Quy |
| 7,249,036 B2 | 7/2007 | Bayne |

(Continued)

*Primary Examiner* — Scott Luan
(74) *Attorney, Agent, or Firm* — The Dobrusin Law Firm, PC (57) ABSTRACT

A garment comprising a central portion including a plurality of electrocardiogram leads, a plurality of auscultation acoustic sensor devices, a flexible respiratory sensor located so that it substantially circumscribes the garment, one or more blood pressure cuff portions located on an at least one arm portion of the garment, wherein the cuff portions are adapted to be loosened and/or tightened and a hardware device for sending and receiving signals via wired or wireless communication.

19 Claims, 4 Drawing Sheets

Related U.S. Application Data on May 29, 2018, provisional application No. 62/741,028, filed on Oct. 4, 2018.

(51) Int. Cl.
  *H04R 3/00* (2006.01)
  *G16H 80/00* (2018.01)
  *A61B 5/022* (2006.01)

(56) References Cited

U.S. PATENT DOCUMENTS

| | | |
|---|---|---|
| 9,208,288 B2 | 12/2015 | Putrino |
| 2002/0111777 A1* | 8/2002 | David ................ A61B 5/04085 |
| | | 702/189 |
| 2009/0171166 A1 | 7/2009 | Amundson et al. |
| 2016/0256104 A1* | 9/2016 | Romem ............. A61B 5/04085 |
| 2018/0132815 A1* | 5/2018 | Tsai ....................... A61B 7/026 |

* cited by examiner

HOME MEDICAL EXAMINATION SYSTEM AND GARMENT

This application claims the benefit of U.S. Provisional Application Nos. 62/625,070, filed Feb. 1, 2018; 62/677,552, filed May 29, 2018; and 62/741,028, filed Oct. 4, 2018, the contents of these applications being hereby incorporated by reference for all purposes.

FIELD OF THE INVENTION

The present invention relates generally to devices and systems for measuring and monitoring vital signs, performing medical physical examinations and electrocardiogram tests to diagnose and treat medical symptoms and conditions in addition to monitoring and treating chronic diseases.

BACKGROUND OF THE INVENTION

The increased cost of health care coupled with increases in population and population age have led to the development of a number of systems for facilitating remote medical treatment in an effort to modernize the health care system by increasing the availability of medical treatment. These systems generally involve a mean for transmitting medical records and/or medical diagnosis data from a patient location to a central medical facility.

As examples, U.S. Pat. Nos. 9,208,288, 7,249,036, 7,156,808 and U.S. Patent Publication No. 2009/0171166 each describe various systems for collecting patient medical data at a first location and transmitting that data to a second location.

In addition, U.S. Patent Publication No. 2016/0256104 describes a garment to be worn on a day-to-day basis that assists in monitoring and transmitting electrocardiogram data.

However, there remains a need for systems for home medical care (or other remote medical care), especially for systems that make it possible for patients that are ill to easily collect accurate vital sign data and conduct a self-exam (or exam by a caregiver or other third party) for a variety of medical conditions. There is a further need for a system that transfers the data from the remote exam (e.g., self-exam) to a home medical computer, any computing device, or a variety of medical facilities and/or individuals who can diagnose and prescribe accordingly across a significant range of medical conditions.

SUMMARY OF THE INVENTION

The present teachings meet one or more of the above needs by providing a garment comprising a central portion including a plurality of electrocardiogram leads, a plurality of auscultation acoustic sensor devices located in one or more of an anterior chest wall, posterior chest wall, anterior abdominal section, posterior abdominal section, or any combination thereof, a flexible respiratory sensor located so that it substantially circumscribes the garment, one or more cuff portions (e.g., blood pressure cuff portions) located on an at least one arm portion of the garment, wherein the cuff portions are adapted to be loosened and/or tightened, and a hardware device for sending and receiving signals via wired or wireless communication.

It is possible that the systems and garment described herein may include one or more of the following aspects. The electrocardiogram leads may include a plurality of precordial leads. The electrocardiogram leads may include one or more limb and one or more precordial leads. The electrocardiogram leads may be attached to a flexible strip of material. The electrocardiogram leads may be disposable. The electrocardiogram leads may be reusable. The electrocardiogram leads may be removably attached to the garment. The electrocardiogram leads may be permanently attached to the garment. The electrocardiogram leads may be attached to a flexible strap and the flexible strap is removably attached to the garment.

The auscultation acoustic sensor devices may include a plurality of microphones, a plurality of stethoscopes, or both. The microphones may be digital microphones adapted for Bluetooth connectivity with one or more computing devices. The one or more computing devices may be selected from a mobile phone, a tablet, a laptop, a computer, a data storage device, any device capable of collecting and/or storing medical records, or any combination thereof. The garment may include at least five, at least ten, at least fifteen, at least twenty, or at least twenty-five digital microphones. The microphones may be surrounded and contained in a pliable rubber or plastic material. The microphones may be located in the front, back and/or sides of the garment. The microphones may be removably attached to the garment. The microphones may be permanently attached to the garment. The microphones may be powered by a portable battery removably attached to the garment. The microphones may be arranged in a grid-like pattern over the anterior chest wall, posterior chest wall, or both. The microphones may be site-specific (e.g. designed for use in a particular location of the garment corresponding to a particular organ location). The microphones may record heart and lung soundwaves which may be then analyzed by software on a computing device. The software may include a special application that is adapted to create functional and anatomical diagrams of a patient's organs (e.g. lungs and heart). These diagrams may outline the findings of the heart and lung soundwaves in terms of location, strength, type, and quality.

The stethoscopes may be digital stethoscopes adapted for Bluetooth connectivity with one or more computing devices. The one or more computing devices may be selected from a mobile phone, a tablet, a laptop, a computer, a data storage device, any device capable of collecting and/or storing medical records, or any combination thereof. The garment may include at least two, at least four, at least six or at least eight electronic stethoscopes. The garment may include one or more anterior stethoscopes and one or more posterior stethoscopes. The garment may include at least two anterior stethoscopes and at least two posterior stethoscopes. The one or more stethoscopes may record heart and lung breathing soundwaves (during normal breathing or when taking deep inspiration) which may then analyzed by software on a computing device.

The respiratory sensor may detect and/or monitor respiratory rate. The respiratory sensor may detect and/or monitor amplitude of respiration. The respiratory sensor may detect and/or monitor respiration rhythm. In addition, the auscultation acoustic sensor devices (e.g., the stethoscopes and/or microphones) may provide the rate, depth and pattern of respiration. The garment may include an instrument removably attached to the garment and adapted for facilitating an abdominal examination. The instrument may be a probe device. The instrument may be attached to the garment via a pocket structure that receives the probe or may be a separate accessory, free of direct attachment to the garment. The garment may include a structure within the garment for receiving one or more of an otoscope, oralscope, ophthalmoscope, PanScope (e.g., a single device that incorporates multiple test devices), ear or oral temperature device, or any combination thereof. The structure may be one or more of a pocket, a strap, a hook, a snap, a flexible band, or any structural fastening device for removably attaching one or more of an otoscope, oralscope, ophthalmoscope, PanScope, oral temperature device, or any combination thereof. The structure may be an attachment for a mobile device (e.g. cellphone; tablet), transforming the mobile device into one or more of an otoscope, oralscope, ophthalmoscope, PanScope, ear or oral temperature device, or any combination thereof. The garment may include one or more of a pocket, a strap, a hook, a snap, a flexible band, or any mechanical fastening device for removably attaching an item to the garment. The garment may include a pulse oximeter removably attached thereto. The item may be one or any combination of an otoscope, oralscope, ophthalmoscope, PanScope or an oral temperature device.

The garment may include a glove removably connected thereto. The glove may include a pulse oximeter located therein. The garment may include a glove removably attached to the garment via one or any combination of a pocket, a strap, a hook, a snap, a flexible band, or any mechanical fastening device.

The garment may include a zipper for opening and closing the garment. The zipper may be centrally located along a torso of a patient. The garment may include sleeves that extend to substantially cover a patient's arms.

The garment may include a PanScope removably attached or in accessory garment package thereto, the PanScope being adapted to record digital images of one or more of the skin, throat, eyes, and ears. The garment may include a device attached thereto that records digital images of one or more of a patient's skin, throat, eyes and ears and the digital images are transmitted to a device which includes software adapted for comparing the digital images to images having known disease states. The device may be an attachment that may be removably attached to a mobile device (e.g. cellphone; tablet). The attachment may transmit images and data to a computing device. The mobile device may be the computing device used to analyze the images and data collected.

The garment may include an abdomen belt integrally formed in the garment or removably attached to the garment. The garment may include an abdomen belt that includes one or more inflatable air compartments for pain location determination. The garment may include an abdomen belt that includes one or more stethoscopes and/or microphones for detecting bowel soundwaves. The garment may include a probe removably attached thereto for performing an abdomen exam. The garment may include a probe removably attached thereto, the probe including one or more of an electronic stethoscope and/or microphone and a pain location sensor. The probe may be controlled and moved by the patient to determine accurately an exact pain location area. The probe may be in direct communication with a computing device by corresponding the location of the probe to a cursor on a screen on a computing device. The garment may include a probe, the probe including a pain location sensor that includes a flexible flapping end for detecting one or more of dullness, tympanicity and organomegaly. The garment may include a probe, the probe including a tenderness location sensor. The garment may include a probe that can be manipulated and moved across the patient's body by the patient or a caregiver. The garment may include a probe adapted for palpation to detect tenderness. The garment may include a probe adapted for palpation to detect rebound tenderness. The garment may include a probe adapted for tapping the surface of the abdomen to deliver percussion. The garment may include a probe adapted for detecting hardness or softness of the abdomen or another part of a patient. The probe may be adapted for locating tenderness in one or more body surface areas including the head, the neck, the chest wall, the limbs, and the back.

The garment may be adapted for transmitting data (e.g., through a wired or wireless connection) acquired from one or more detection devices located on or with the garment to one or more computing devices, said computing devices being accessible by one or more of a home medical doctor computer device, a physician office (e.g., a physician, a physician's assistant, a nurse practitioner, a nurse, a medical resident, a medical assistant, a medical billing associate, or other medical office staff), a pharmacy, a caretaker, a family member, an emergency medical treatment professional, an insurance company, or any individual who may take an action based upon the data.

The garment may be formed in a plurality of sizes, including sizes for children, small adults, medium adults and large adults so that the garment fits in a form fitting manner for accurate detection of vital signs.

The teachings herein further provide for a method comprising: providing a garment to a patient, the garment including one or more microphones connected thereto, the microphones designed to be site-specific (e.g. designed for use in a particular location of the garment corresponding to a particular organ region); adjusting the garment so that the microphones are able to obtain soundwaves indicative of one or more patient vital signs; obtaining the soundwaves from the patient; filtering, buffering and/or amplifying the soundwaves to produce a signal; optionally converting the signal from analog format to digital format; filtering the signal; normalizing the signal; analyzing the normalized signal and/or classifying higher order patterns to be transmitted as diagnostic data; and transmitting the diagnostic data to a device capable of receiving the diagnostic data.

The teachings herein are also directed to a method comprising providing a garment to a patient for wearing around the patient's torso, locating the garment around the patient's torso so that it is form fitting and substantially prevented from significant movement about the patient's body, securing one or more detection devices so that they are in direct contact with the patient's skin, and measuring one or more vital signs of the patient via the one or more detection devices.

DETAILED DESCRIPTION

The explanations and illustrations presented herein are intended to acquaint others skilled in the art with the invention, its principles, and its practical application. The specific embodiments of the present invention as set forth are not intended as being exhaustive or limiting of the invention. The scope of the invention should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings pertain generally to improved devices and systems for remote medical care including identifying and measuring an extensive range of vital and physical examination signs. The garment may provide for an initial medical evaluation system that provides initial key medical data to on site (home) medical software or an offsite physician or the like. The devices and systems described herein may further include solutions for transmitting any data collected from a patient to a desired medical facility and/or professional. The garment described herein may be utilized by any patient desiring examination and treatment for most medical conditions while remaining in the comfort of their own home. The patient self-testing may provide as thorough or a more thorough analysis than an in-office doctor visit. The results of the self-exam can be easily transmitted to the home medical software or a medical professional where it can be determined if further tests are required, a prescription is required, a specialist is required or if immediate medical attention is necessary.

The garment may be shaped as a jacket, a vest, a wrap, a poncho, or the like. The garment may include a plurality of electrocardiogram leads, a plurality of auscultation acoustic sensor devices located in one or more of an anterior chest wall, posterior chest wall, anterior abdominal section, posterior abdominal section, or any combination thereof to provide optimal heart and lungs auscultation, a flexible respiratory sensor, one or more cuff portions (e.g., blood pressure cuff portions) located on an at least one arm portion of the garment, and a hardware device for sending and receiving signals via wired or wireless communication. The garment may include a section that contacts a patient's abdomen. The garment may include a section that contacts a patient's lower back. The garment may include a plurality of devices that are removably connected to or work in tandem with the garment. These devices may include but are not limited to a pulse oximeter, otoscope, oralscope, ophthalmoscope, PanScope, oral temperature device.

The PanScope or any similar digital imaging device may be utilized to take photos of one or more of a patient's skin, throat, eyes, ears, or nose. These images may then be compared to via a software program to a catalog of stored images in an effort to aid in diagnosis.

The auscultation acoustic sensor devices (e.g. microphones; stethoscopes) may be arranged in a manner which forms a blanket that hugs the patient thorax providing optimal heart and lungs auscultation. The auscultation acoustic sensor devices (e.g. microphones; stethoscopes) may be utilized to record one or more of a patient's lung sounds including but not limited to clear breathing sounds, reduced breathing sounds, diffuse wheezing, basilar crackles, and scattered rhonchi, or absence of breathing sounds. The auscultation acoustic sensor devices (e.g. microphones; stethoscopes) may be utilized to record one or more of a patient's heart sounds including but not limited to normal heart sounds, S1 heart sound, S2 heart sound, murmurs, aortic stenosis, mitral regurgitation, pulmonic stenosis, and aortic insufficiency. The auscultation acoustic sensor devices may provide a description of the location, strength, type, and quality of the recorded sound. The auscultation acoustic sensor devices may be individually numbered in the garment to aid in determining the location of the lung and heart sounds.

The electrocardiogram leads may be integrated into the garment or may be located onto a separate undergarment that is worn between a patient's skin and the garment. The electrocardiogram leads may be housed on one or more straps that locate each lead in the correct location on a patient's body. The electrocardiogram leads may be arranged in the same manner as a traditional 12-lead or 24-lead electrocardiogram test. The electrocardiogram leads may include an adhesive. The electrocardiogram leads may be disposable or may be reusable. The electrocardiogram leads may be integrally formed with or removably attached to a strap, and the strap may be embedded in the garment or may be separately formed from the garment. The strap may be removably attached to the garment.

The blood pressure cuff portions may be tightened (e.g., may be tightened by Velcro) in order to measure a patient's blood pressure. The cuff portions may be embedded in the garment or may be removably attached to the garment.

The respiratory sensor may detect and/or monitor one or more of respiratory rate, amplitude of respiration, and respiration rhythm. It is possible that the respiratory sensor may be utilized to perform a sleep study. The garment and system may also allow patients to have in-home stress tests, which may include use of a treadmill or other exercise apparatus. The system may also include a helmet with EEG sensors (to record brain waves) that can help in seizure evaluation.

One or more of the pulse oximeter, otoscope, oralscope, ophthalmoscope, PanScope, or oral temperature device may be adapted to directly transmit data to a computing device. One or more of the pulse oximeter, otoscope, oralscope, ophthalmoscope, PanScope, or oral temperature device may be adapted to directly transmit data to hardware associated with the garment which then transmits to a computing device. The one or more pulse oximeter, otoscope, oralscope, ophthalmoscope, PanScope, oral or ear temperature device, or a combination thereof may be a removeable attachment that connects to a mobile device (e.g. cellphone; tablet). The mobile device may include a special application that allows the attachment device to connect with the mobile device, turning the mobile device into one or more pulse oximeter, otoscope, oralscope, ophthalmoscope, PanScope, oral or ear temperature device, or a combination thereof. The attachment may work in conjunction with a camera located in the mobile device. The attachment may include a lens that is positioned over the camera of the mobile device to amplify images in greater detail. The mobile device may transmit images and data to a computing device. The mobile device may be the computing device with which the attachment, the garment, or both transmit data and images.

The data collected by one or more of the devices associated with the garment may be converted and/or processed prior to transmitting to a computing device. The data collected by one or more of the devices associated with the garment may be converted and/or processed after transmitting to a computing device such that the computing device performs the processing/conversion steps. As one non-limiting example, data from a plurality of microphones may undergo filtering, buffering and/or amplifying of the soundwaves to produce a signal. The signal may then be converted from analog format to digital format. The signal may then be filtered. The signal may then be normalized. At that point, the normalized signal may be analyzed and transmitted.

The garment may include an abdomen belt integrally formed in the garment or removably attached to the garment. The abdomen belt may include one or more inflatable air compartments. The abdomen belt may include one or more stethoscopes for detecting bowel soundwaves. The garment may include a probe removably attached thereto for performing an abdomen exam.

The garment may include a probe. The probe may include one or more of an electronic stethoscope and a pain location sensor. The pain location sensor may include a flexible flapping end. The probe may include a tenderness location sensor (interactive exam). The probe may be adapted for palpation movement. The probe may be adapted for palpation to detect rebound tenderness. The probe may be adapted for locating tenderness in one or more of the head, chest wall, limbs, and back of a patient.

The garment may be adapted for transmitting data (e.g., through a wired or wireless connection). The data may be collected and may optionally be stored on a hardware device associated with the garment which may be a computing device or which may transfer data to a computing device. Any of the detection devices described herein (the stethoscope, the microphone, the electrocardiogram leads, the probe, the pulse oximeter, otoscope, oralscope, ophthalmoscope, PanScope, oral temperature device) may facilitate collection of data and may be adapted to transmit the data to a hardware associated with the garment. Alternatively, any of the detection devices described herein may be adapted to transmit data directly to a computing device.

The computing devices and/or the data gathered by the one or more detection devices may be accessible by one or more of a physician office (e.g., a physician, a physician's assistant, a nurse practitioner, a nurse, a medical resident, a medical assistant, a medical billing associate, or other medical office staff), a pharmacy, a caretaker, a family member, an emergency medical treatment professional, an insurance company, or any individual who may take an action based upon the data. The office and/or individual receiving the data is then able to make medical diagnosis decisions based upon the data. It is possible that the home computing device may also replace the human doctor as it may be programmed so that it can establish a diagnosis, recommend testing and/or prescribe medications.

The garment may be associated with one or more of an electronic scale and measuring device for providing a patient's weight and height respectively, which may be important for medicine dosing. The garment may be available in a variety of sizes so that it capable of close fitting each patient. The garment may be modified for use with infants and/or small children. As the garment may be specifically well suited for in-home use it may be accompanied by a variety of test kits including but not limited to glucose tests, pregnancy tests, influenza tests, strep tests, mononucleosis tests, and urine tests. The garment may be accompanied by a respiratory flow meter.

It is possible that for infants or small children, the system may not include a garment but the system includes a single digital stethoscope and/or microphone, a PanScope, a pulse oximeter and an ear thermometer. The ear temperature may be obtained using the ear thermometer. The heart rate and oxygen saturation may be measured by pulse oximetry. By placing the stethoscope and/or microphone at designated spots in anterior and posterior chest, breath and heart sounds are recorded and the respiratory rate can be measured as well.

The garment may be located onto a patient with no additional assistance. The garment may include one or more fasteners or zippers so that the garment is tight fitting on the patient and the devices associated with the garment are in contact with the patient as necessary to register necessary patient data. The garment may include an indicator to notify the patient that one or more devices should be adjusted for accurate data to be collected.

The devices associated with the garment may be embedded in the garment or removably attached to the garment. The devices may be located into pockets formed on the garment. The devices may be fastened to the garment by one or more of a strap, a hook, a snap, a flexible band, or any mechanical fastening device.

Figure 1:
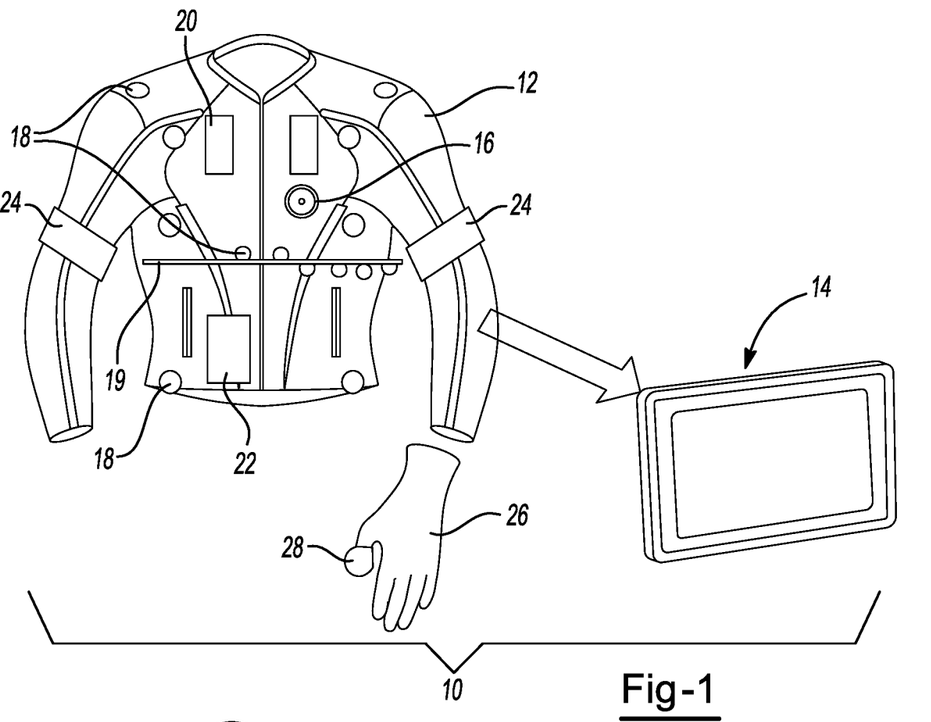
FIG. 1 is a perspective view of an illustrative garment in accordance with the present teachings.

As shown in more detail in FIG. 1, the system 10 is shown to include a garment 12 and a computing device 14. The garment 12 includes a plurality of stethoscopes 16 and a plurality of electrocardiogram leads 18. The garment 12 further includes a respiratory sensor 19. An oral temperature probe pocket 20 is shown for locating a temperature probe therein. An abdomen probe pocket 22 is also shown for locating an abdomen probe therein. Each arm is shown to include a blood pressure cuff portion 24. A glove 26 is also shown including a pulse oximeter 28.

Figure 2:
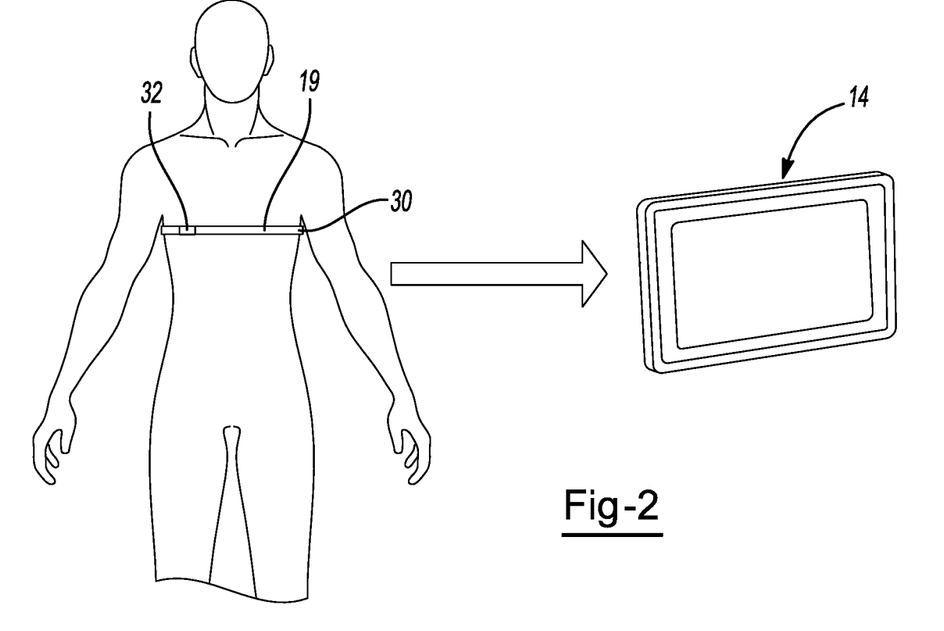
FIG. 2 is a perspective view of an illustrative respiratory sensor in accordance with the present teachings.

FIG. 2 depicts the respiratory sensor 18 including a band portion 30 and kinetic sensor 32. The band portion 30 is shown substantially circumscribing a patient's upper torso and the kinetic sensor 32 is shown in the upper right quadrant of the patient's torso.

Figure 3:
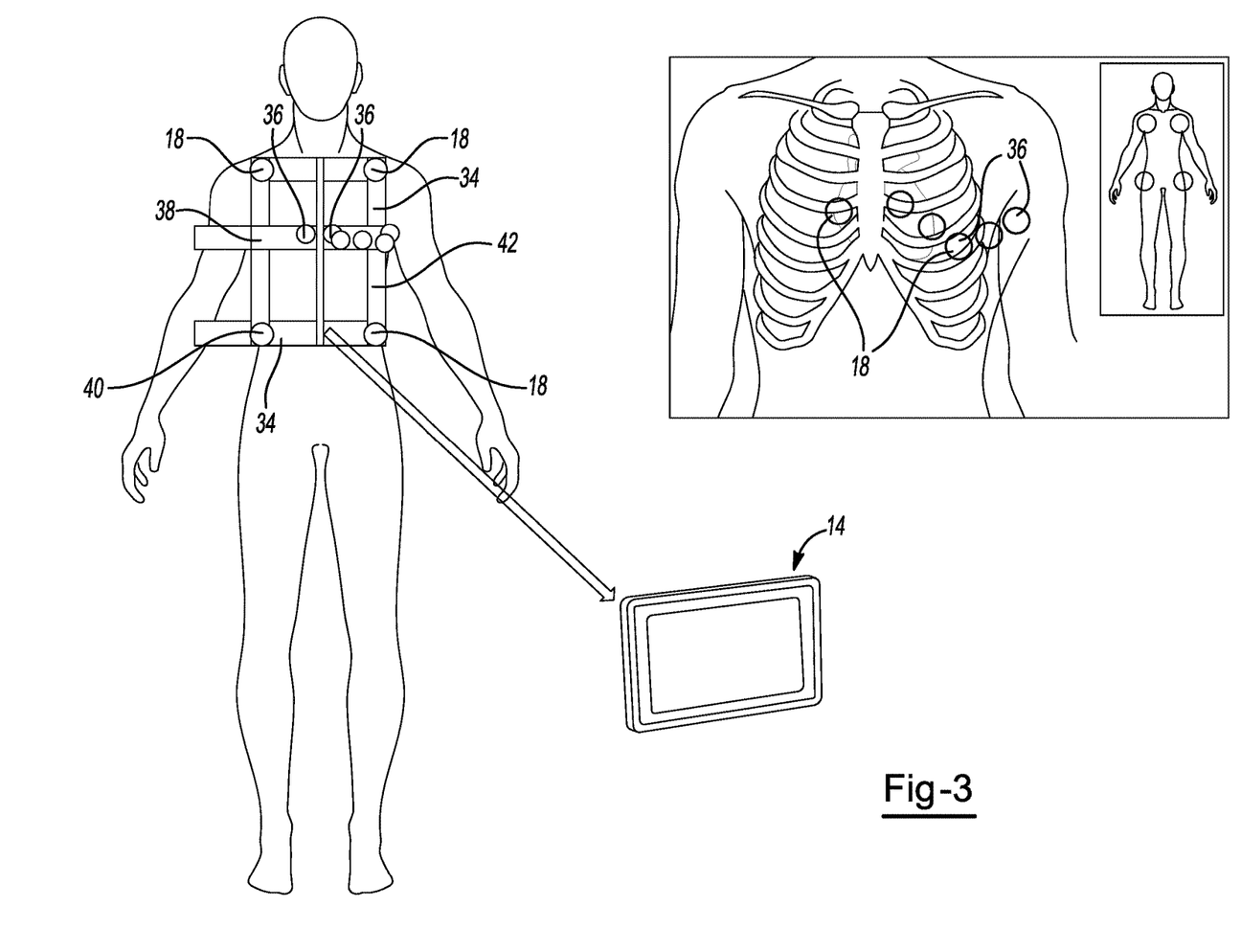
FIG. 3 is a perspective view of an illustrative electrocardiogram lead arrangement in a garment in accordance with the present teachings.

As shown for example in FIG. 3, the electrocardiogram leads 18 may be embedded in the garment in an arrangement as shown. A plurality of straps 34 may carry the leads 18 so that the precordial leads 36 are located along a strap 38 that runs horizontal across a patient's torso, whereas the limb leads 40 are located along a strap 42 that runs vertically from a patient's shoulders to hips.

Figure 4:
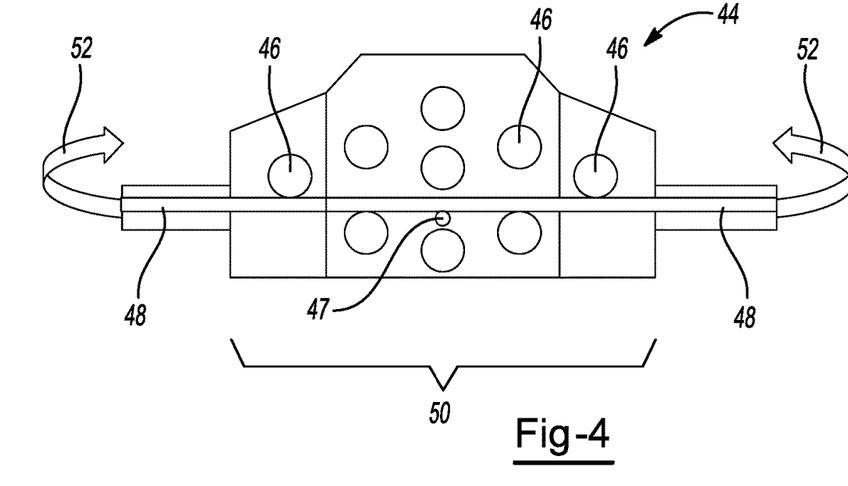
FIG. 4 is a perspective view of an illustrative abdomen belt in accordance with the present teachings.

As shown in FIG. 4, the garment may include an abdomen belt 44. The abdomen belt 44 includes a plurality of inflatable air compartments 46 for filling with air to identify locations of pain and/or discomfort. The abdomen belt 44 also includes a centrally located stethoscope 47 for registering bowel sounds. A tension sensor 48 may also be formed along the abdomen belt 44. The abdomen belt is shown to include a central portion 50 for housing the air compartments 46 and a belt portion 52 for locating the abdomen belt 44 around a patient's back.

Figure 5:
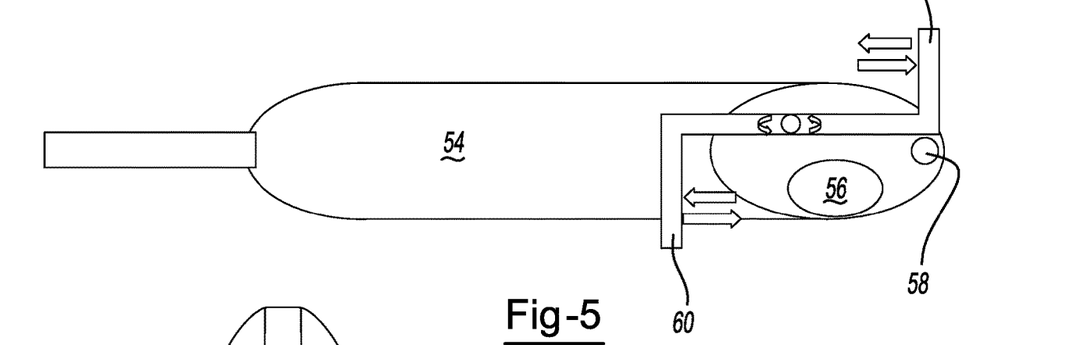
FIG. 5 is a perspective view of an illustrative probe in accordance with the present teachings.

FIG. 5 shows an exemplary probe 54 for use in association with the garment. The probe 54 includes a stethoscope 56. The probe 54 also includes a pain location sensor 58. A flapping portion 60 is also included on the probe 54 for detecting percussion of the abdomen by tapping with the flapping portion 60.

Figure 6:
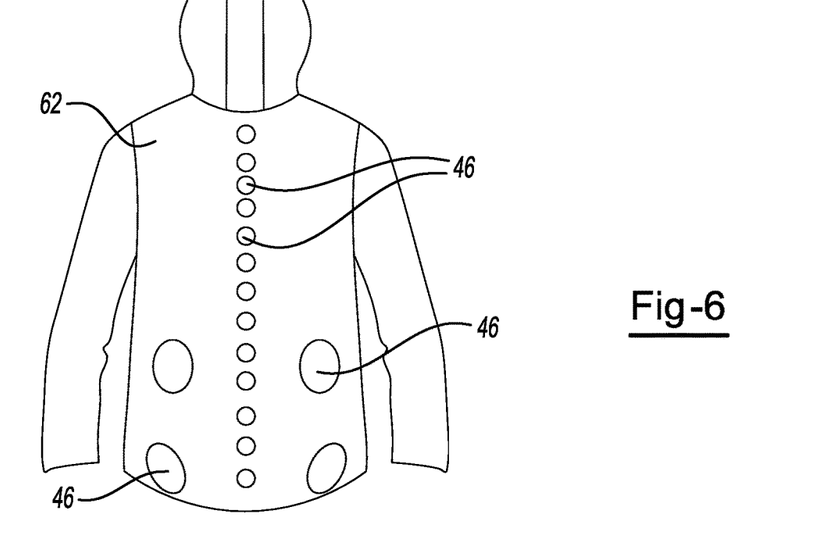
FIG. 6 is a back view of an illustrative garment in accordance with the present teachings.

As shown in FIG. 6, the back of the garment 62 may be fitted with a plurality of air compartments 46 for locating pain locations along a patient's back.

Figure 7:
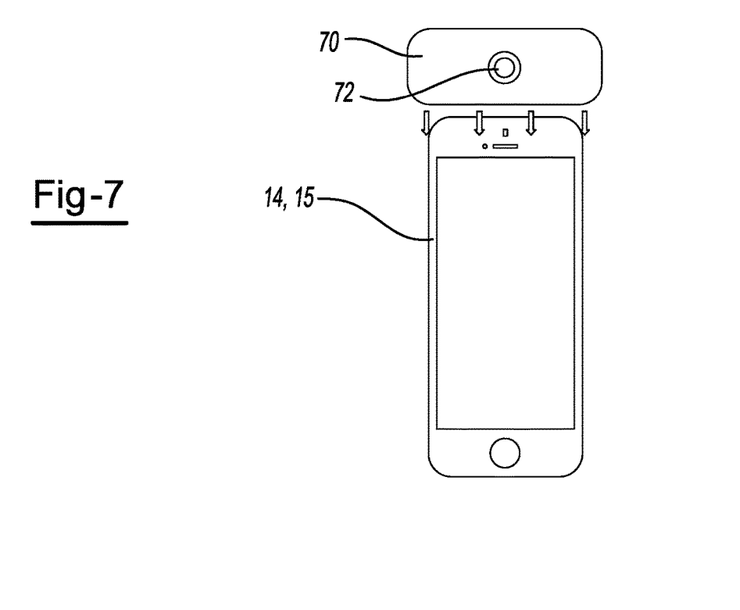
FIG. 7 is a perspective view of an examination attachment for a mobile device in accordance with the present teachings.

FIG. 7 shows a mobile device 15 with an attachment 70. The attachment 70 includes a lens 72 for gathering images. The lens 72 works in conjunction with a camera (not shown) of the mobile device 15 to convert the mobile device into one or more of an otoscope, oralscope, ophthalmoscope, PanScope, ear or oral temperature device, or any combination thereof. Additionally, in this embodiment, the mobile device 15 is the computing device 14.

Figure 8:
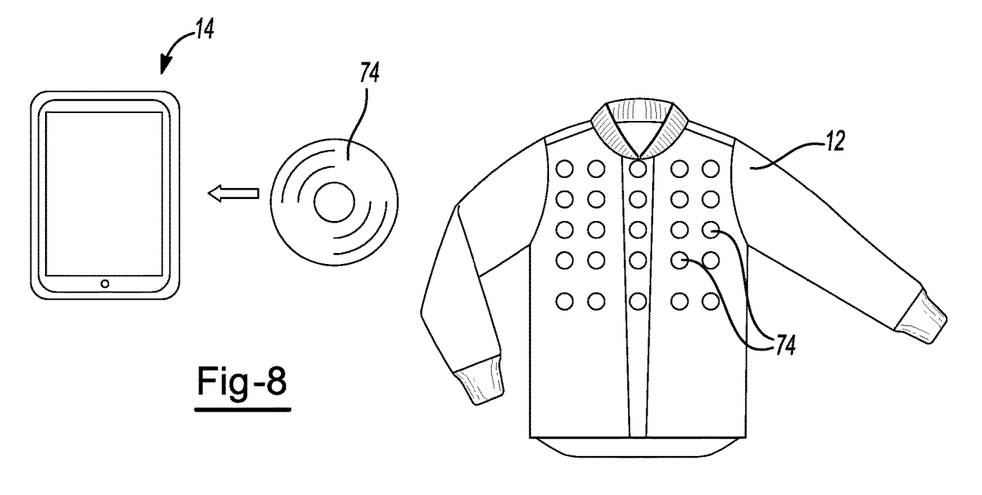
FIG. 8 is a perspective view of an illustrative microphone arrangement in a garment in accordance with the present teachings.

FIG. 8 shows a front-view of an exemplary garment 12. The garment 12 includes a plurality of microphones 74 in a grid-like pattern. The microphones 74 record lung and/or heart soundwaves for transmittal and analyzation on the computing device 14.

As to all of the foregoing general teachings, as used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. Concentrations of ingredients identified in Tables herein may vary ±10%, or even 20% or more and remain within the teachings.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. A garment comprising:
   a) a central portion including a plurality of electrocardiogram leads;
   b) a plurality of auscultation acoustic sensor devices located in one or more of an anterior chest wall, posterior chest wall, anterior abdominal section, posterior abdominal section, or any combination thereof;
   c) a flexible respiratory sensor located so that it substantially circumscribes the garment;
   d) one or more cuff portions located on an at least one arm portion of the garment, wherein the cuff portions are adapted to be loosened and/or tightened for measuring blood pressure; and
   e) a hardware device for sending and receiving signals via wired or wireless communication
   f) an abdomen belt integrally formed or removably attached to the garment, the abdomen belt including one or more inflatable air compartments for pain location determination.

2. The garment of claim 1, wherein the auscultation acoustic sensor devices include a plurality of stethoscopes, a plurality of microphones, or both for recording heart and lung soundwaves.

3. The garment of claim 2, wherein the recorded heart and lung soundwaves are analyzed by software on one or more computing devices, and wherein the one or more computing devices are selected from a mobile phone, a tablet, a laptop, a computer, a data storage device, any device capable of collecting and/or storing medical records, or any combination thereof.

4. The garment of claim 3, wherein the microphones are digital microphones adapted for Bluetooth connectivity with the one or more computing devices.

5. The garment of claim 4, wherein the software is adapted to create functional and anatomical diagrams of a patient's lungs and heart.

6. The garment of claim 4, wherein the garment includes at least five, at least ten, at least fifteen, at least twenty, or at least twenty-five digital microphones.

7. The garment of claim 6, wherein the microphones are arranged in a grid-like pattern over a patient's anterior chest wall and/or posterior chest wall for optimal heart and lungs auscultation.

8. The garment of claim 7, wherein the microphones are site-specific.

9. The garment of claim 8, wherein the microphones are contained in a pliable rubber and/or plastic material.

10. The garment of claim 8, wherein the microphones are imbedded in the garment.

11. The garment of claim 8, wherein the microphones are removably attached to the garment.

12. The garment of claim 1, wherein the abdomen belt includes a probe device removably attached thereto for performing an abdominal examination.

13. The garment of claim 12, wherein the probe includes one or more of a stethoscope, microphone, a device that contacts the user.

14. The garment of claim 13, wherein the stethoscope, microphone, or both detect bowel soundwaves.

15. The garment of claim 12, wherein a device that contacts the user includes a flexible flapping end for detecting one or more of dullness, tympanicity and organomegaly.

16. The garment of claim 1, including a structure within the garment for receiving one or more of an otoscope, oralscope, ophthalmoscope, PanScope, oral temperature device, or any combination thereof.

17. The garment of claim 1, wherein the garment is formed in a plurality of sizes, including sizes for children, small adults, medium adults and large adults so that the garment fits in a form fitting manner for accurate detection of vital signs.

18. The garment of claim 1, wherein the garment is adapted for transmitting data (e.g., through a wired or wireless connection) acquired from one or more of the stethoscopes, the microphones, the electrocardiogram leads, the probe, the pulse oximeter, otoscope, oralscope, ophthalmoscope, PanScope, and oral temperature device located on or with the garment to home medical computer device or other computing devices, said computing devices being accessible by one or more of a physician office, a pharmacy, a caretaker, a family member, an emergency medical treatment professional, an insurance company, or any individual who may take an action based upon the data.

19. A method comprising:
providing the garment of claim 1 to a patient, the garment including one or more digital microphones connected thereto, the microphones adapted to be designed for use in a particular location of the garment corresponding to a particular organ region;
adjusting the garment so that the microphones are able to obtain soundwaves indicative of one or more patient vital signs;
obtaining the soundwaves from the patient;
filtering, buffering and/or amplifying the soundwaves to produce a signal;
optionally converting the signal from analog format to digital format;
filtering the signal;
normalizing the signal;
analyzing the normalized signal and/or classifying higher order patterns to be transmitted as diagnostic data;
transmitting the diagnostic data to a device capable of receiving the diagnostic data.

* * * * *